(12) United States Patent
Constable et al.

(10) Patent No.: US 11,320,505 B2
(45) Date of Patent: May 3, 2022

(54) MRI SYSTEM USING NONUNIFORM MAGNETIC FIELDS

(71) Applicant: Yale University, New Haven, CT (US)

(72) Inventors: Robert T. Constable, Madison, CT (US); Yuqing Wan, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/465,389

(22) PCT Filed: Dec. 6, 2017

(86) PCT No.: PCT/US2017/064830
§ 371 (c)(1),
(2) Date: May 30, 2019

(87) PCT Pub. No.: WO2018/106760
PCT Pub. Date: Jun. 14, 2018

(65) Prior Publication Data
US 2020/0003856 A1    Jan. 2, 2020

Related U.S. Application Data

(60) Provisional application No. 62/430,594, filed on Dec. 6, 2016.

(51) Int. Cl.
*G01R 33/44* (2006.01)
*G01R 33/24* (2006.01)
(Continued)

(52) U.S. Cl.
CPC .......... *G01R 33/445* (2013.01); *G01R 33/24* (2013.01); *G01R 33/287* (2013.01); *A61B 5/055* (2013.01); *G01R 33/02* (2013.01)

(58) Field of Classification Search
None
See application file for complete search history.

(56) References Cited

U.S. PATENT DOCUMENTS 5,184,075 A * 2/1993 Nishimura ............. G01R 33/24
324/309
5,798,680 A * 8/1998 Abele ................ G01R 33/3806
324/320

(Continued)

*Primary Examiner* — Nasima Monsur
(74) *Attorney, Agent, or Firm* — Lumen Patent Firm

(57) ABSTRACT

A method for magnetic resonance imaging uses an electromagnet [304], which may have open geometry, to generate a spatially nonuniform magnetic field within an imaging region [306]. The current through the electromagnet is controlled to repeatedly cycle the nonuniform magnetic field between a high strength for polarizing spins and a low strength for spatial encoding and readout. Using RF coils [308], excitation pulses are generated at a frequency that selects a non-planar isofield slice for imaging. The RF coils are also used to generate refocusing pulses for imaging and to generate spatial encoding pulses, which may be nonlinear. Magnetic resonance signals originating from the selected non-planar isofield slice of the nonuniform magnetic field in the imaging region [306] are detected using the RF coils [308] in parallel receive mode. MRI images are reconstructed from the parallel received magnetic resonance signals, e.g., using algebraic reconstruction.

12 Claims, 10 Drawing Sheets

(51) Int. Cl.
*G01R 33/28* (2006.01)
*A61B 5/055* (2006.01)
*G01R 33/02* (2006.01)

(56) References Cited

U.S. PATENT DOCUMENTS

| | | |
|---|---|---|
| 8,710,839 B2 | 4/2014 | Constable |
| 9,229,081 B2 | 1/2016 | Constable |
| 2006/0273792 A1* | 12/2006 | Kholmovski ...... G01R 33/5611 324/309 |
| 2010/0237861 A1* | 9/2010 | Hennel ................ G01R 33/246 324/307 |
| 2010/0259259 A1* | 10/2010 | Zahn ................. G01R 33/5601 324/309 |
| 2010/0259263 A1* | 10/2010 | Holland ................ A61B 5/055 324/310 |
| 2016/0231409 A1 | 8/2016 | Taviani |
| 2016/0291112 A1 | 10/2016 | Constable |
| 2017/0261574 A1* | 9/2017 | Stainsby ................ H01F 6/008 |
| 2019/0162807 A1 | 5/2019 | Zahneisen |

\* cited by examiner

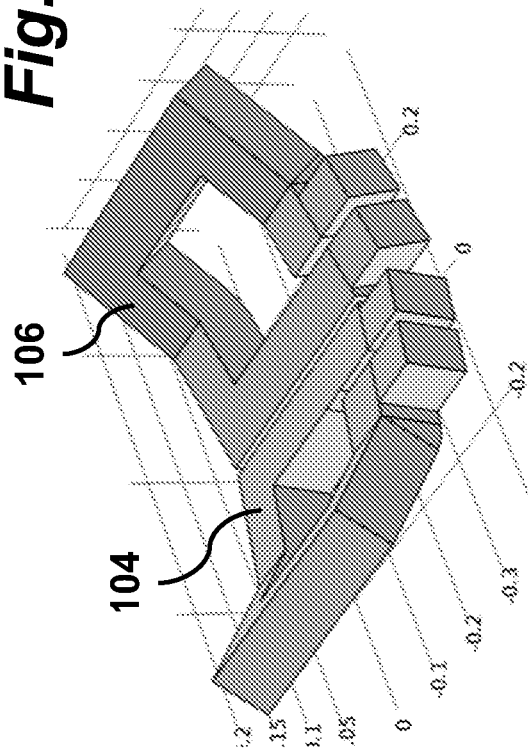
Fig. 1A
Fig. 1B
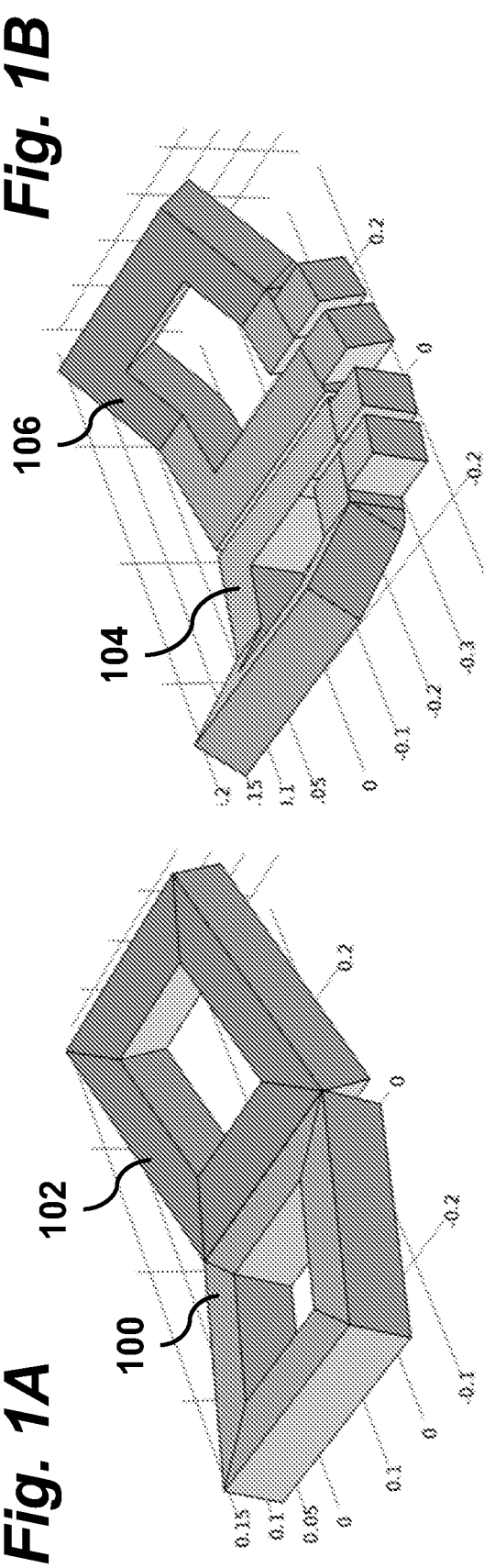
Fig. 1C
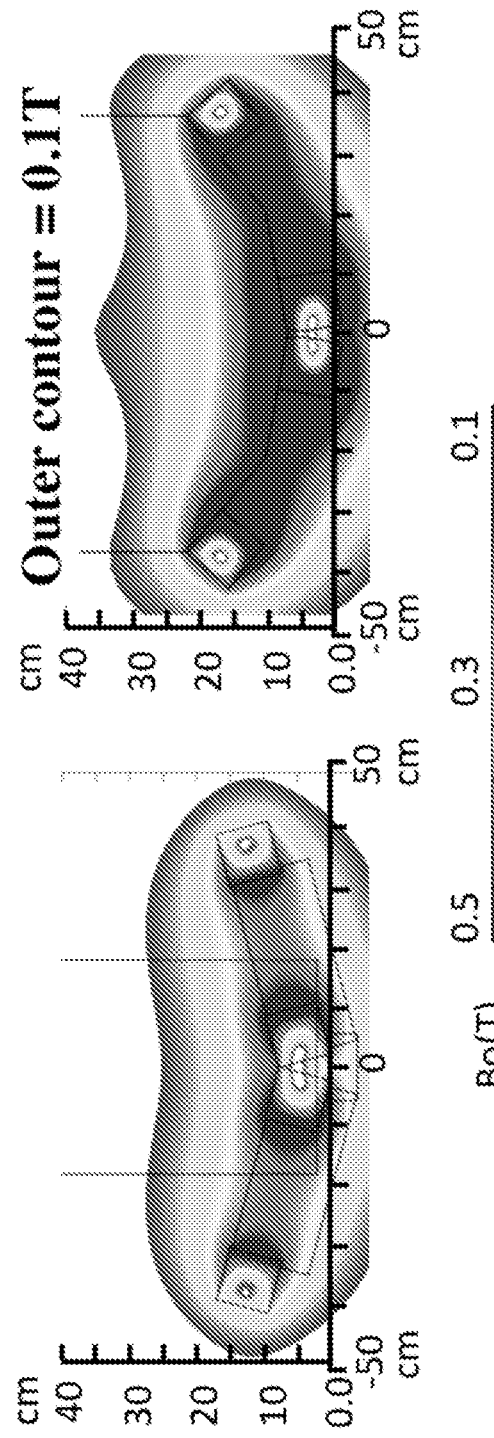
Fig. 1D

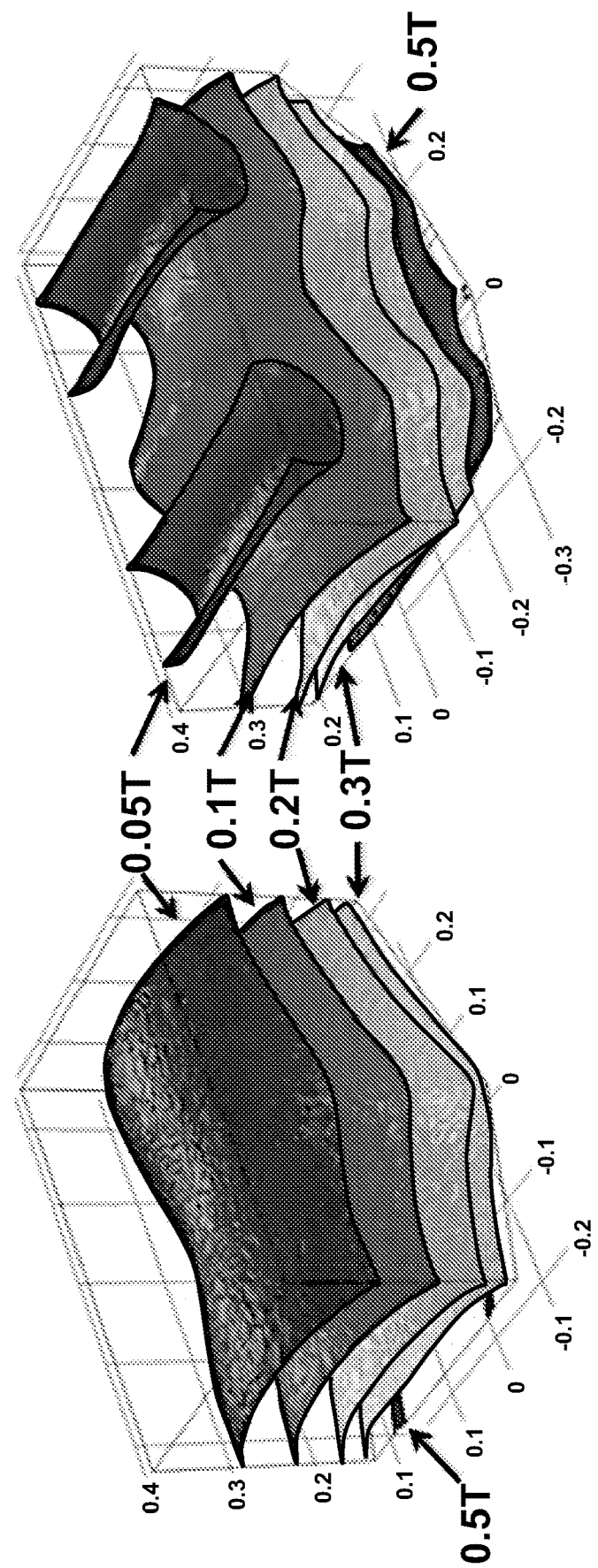

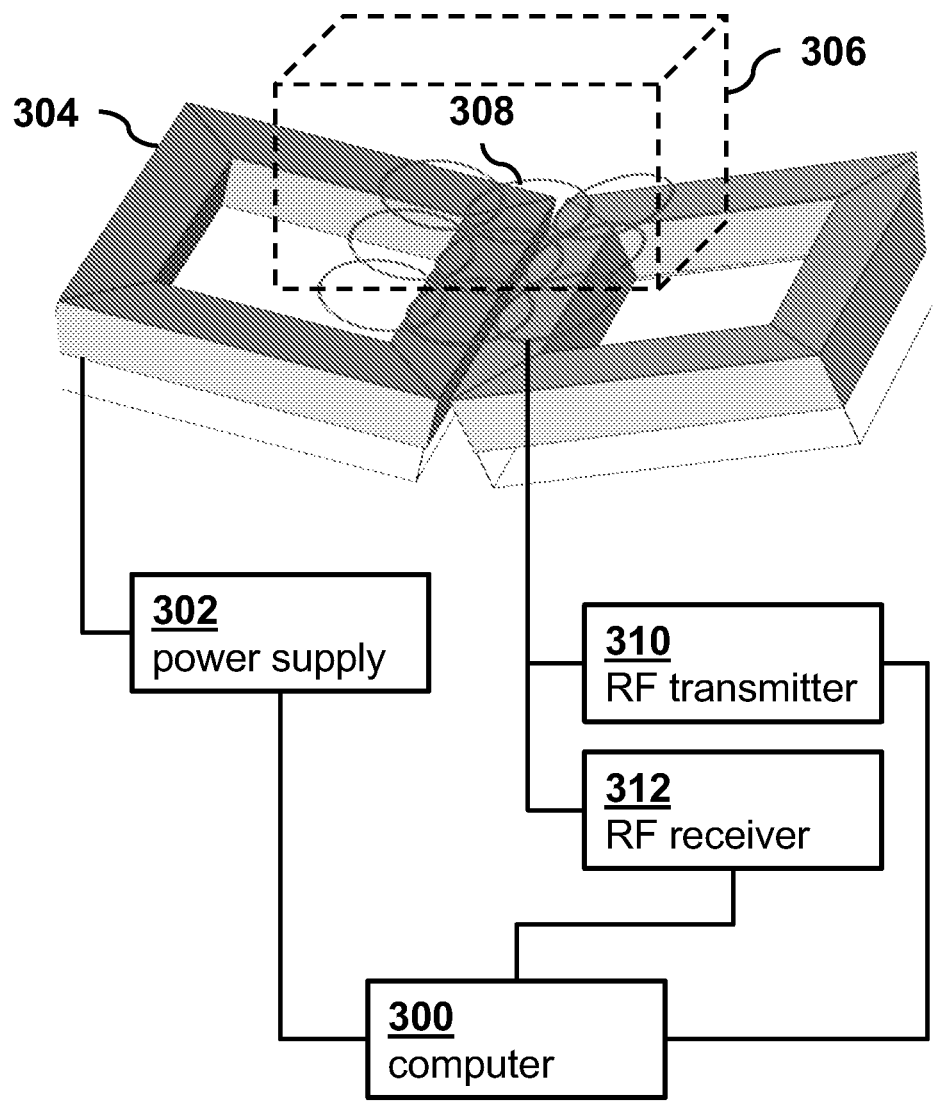

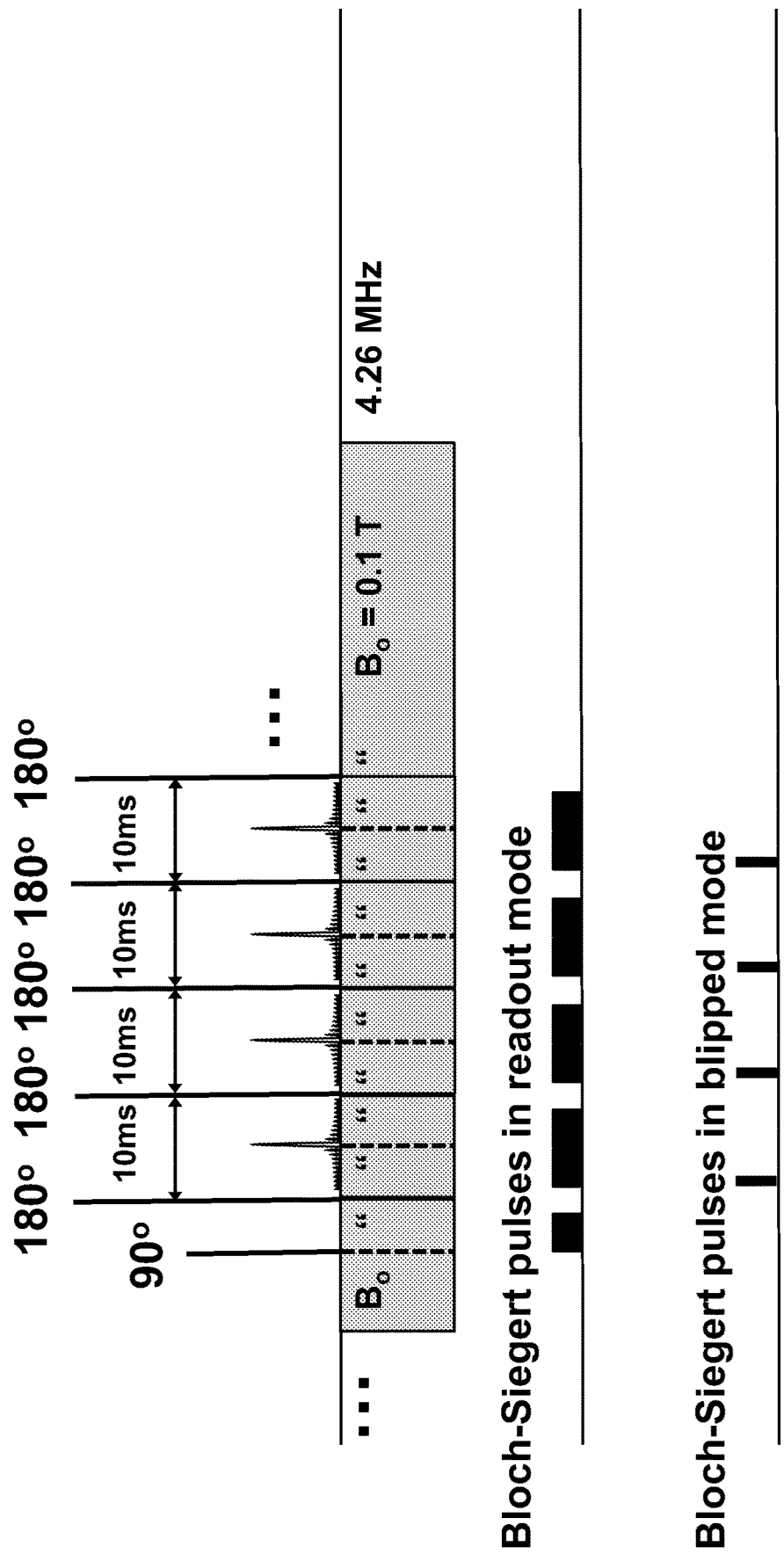

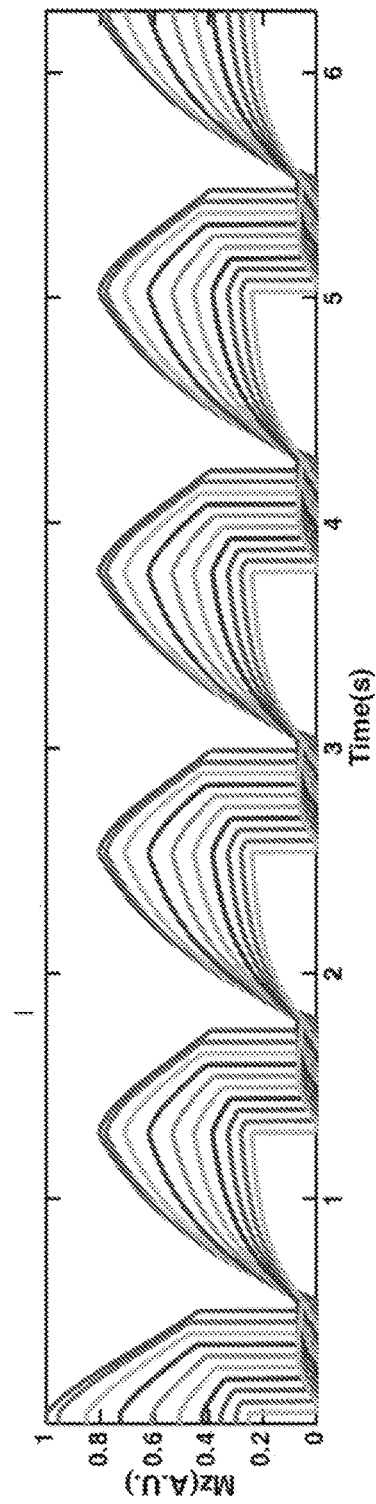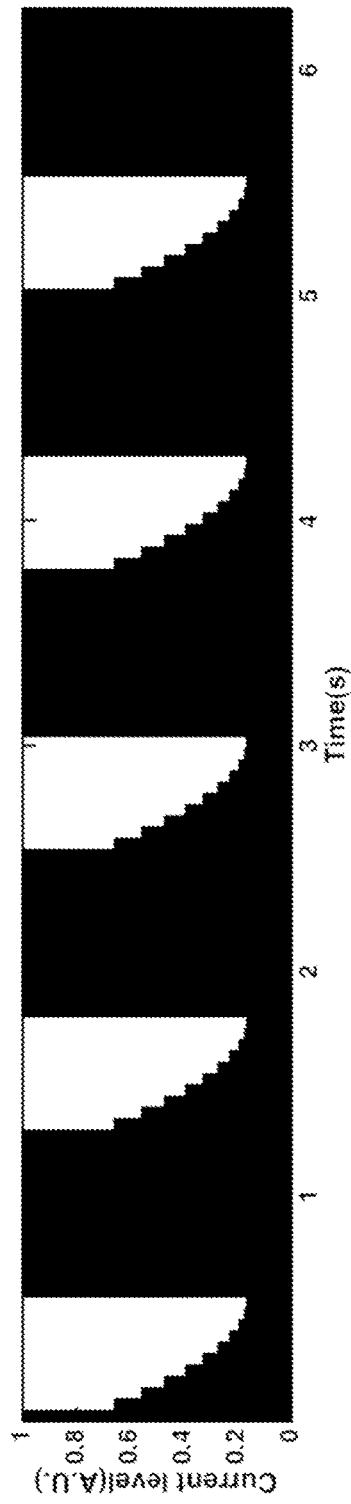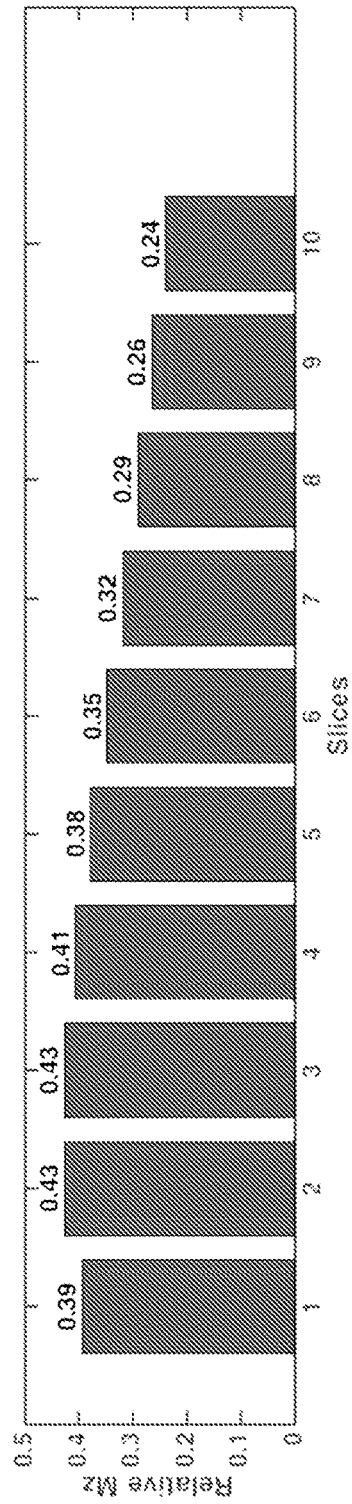

MRI SYSTEM USING NONUNIFORM MAGNETIC FIELDS

CROSS-REFERENCE TO RELATED APPLICATIONS

This application is a 371 of PCT application PCT/US2017/064830 filed Dec. 6, 2017. PCT application PCT/US2017/064830 claims the benefit of U.S. Provisional application 62/430,594 filed Dec. 6, 2016.

FIELD OF THE INVENTION

The present invention relates generally to systems and methods for diagnostic imaging. More specifically, it relates to devices and techniques for magnetic resonance imaging.

BACKGROUND OF THE INVENTION

In conventional magnetic resonance imaging (MRI) systems, a spatially uniform main magnetic field is needed in the imaging region because large field gradients dephase the signal before it can be acquired. This requirement of conventional MRI severely limits the design opportunities of the main magnet, and the dependence on linear gradient fields for spatial encoding also constrains the designs. In both cases, this typically leads to an MRI system with large, cylindrically shaped magnets surrounding an examination table where the patient is positioned. This closed design of the magnet is not suitable for imaging claustrophobic patients and does not allow easy medical interventions or imaging of obese individuals. Conventional MRI systems are also very expensive. The high manufacture and operational cost associated with building superconducting magnets with uniform magnet fields prevents widespread availability of MR imaging, especially for MR as an initial screening tool. It would be an advance in the art to provide an MRI imaging system and technique that overcomes these limitations of conventional MRI.

SUMMARY OF THE INVENTION

Significantly, the inventors have discovered an MRI system and technique that makes practical, for the first time, the ability to obtain MR images using a nonuniform main magnetic field. The ability to perform MRI using a nonuniform main magnetic field allows the MRI system to have an open magnet design, which has many practical advantages. The system is potentially inexpensive because of the relaxed construction requirements in building a magnet that does not need to generate a uniform main magnetic field; the system is quiet because no gradient coils are required; and the open magnet design allows scanning of claustrophobic subjects. The open design also allows a compact MRI system having wider range of shapes and sizes. For example, it allows a small MRI system to be built into an examination table or wall. A vertical design could be dedicated to weighted-spine imaging. Other small devices could be designed for specific applications in imaging the brain, breast scanning, or gynecologic applications. This allows physicians to perform preliminary scanning in the doctor's office or in the field, similar to how ultrasound imaging is used today, making it widely accessible in doctor's offices. Portable MRI systems are also envisioned. The technique also can be applied to MR based material analysis, MR spectroscopy, and solid material NMR.

These advantages are made possible by a combination of innovative techniques that liberate MRI from the requirement of a uniform main magnetic field. In contrast with conventional MRI, the MRI technique of the present invention can provide high quality images using a nonuniform main magnetic field. This is enabled by using an electromagnet to generate and cycle a nonuniform main magnetic field between a high field for spin polarization and a lower field for slice selection and MR signal readout, and using multicoil arrays for excitation, spin-manipulation, spatial encoding and receiving the MR signals. The use of RF for spatial encoding using the Bloch-Siegert shift and the main field shape eliminates the need for linear gradient coils. The image is reconstructed using reconstruction techniques and parallel imaging.

In one aspect, the invention provides a method for magnetic resonance imaging. An electromagnet is used to generate a spatially nonuniform magnetic field within an imaging region. By controlling current through the electromagnet, the nonuniform magnetic field is repeatedly cycled between a first strength for polarizing spins and a second strength, lower than the first strength, for spatial encoding and readout. Using RF coils, excitation pulses are generated at a frequency that selects a non-planar isofield slice for imaging. The RF coils are also used to generate refocusing pulses for imaging and to generate spatial encoding pulses. Magnetic resonance signals originating from the selected non-planar isofield slice of the nonuniform magnetic field in the imaging region are detected using the RF coils in parallel receive mode. MRI images are reconstructed from the parallel received magnetic resonance signals.

The nonuniform magnetic field preferably has a spatial variation of more than 5 ppm within the imaging region.

The electromagnet may be an open-geometry electromagnet that extends around the imaging region by no more than 270 degrees.

The first strength for polarizing spins may be at least 0.2 T and the second strength for spatial encoding and readout may be at most 0.1 T. In some embodiments, the first strength may be at least 0.6 T and the second strength for spatial encoding and readout may be at most 0.1 T.

In some embodiments, the RF coils comprise a phased array of coils.

The spatial encoding may be nonlinear spatial encoding. The spatial encoding may be generated via the Bloch-Siegert shift or other spatial encoding pulses.

The refocusing pulses generated using RF coils may include 180-degree RF pulses inserted to refocus the effects of the residual static gradient fields.

In some embodiments, the RF coils may comprise first and second subsets of coils with no common coils, and spatial encoding is generated using the first subset of the RF coils, while selecting a non-planar isofield slice and detecting magnetic resonance signals using the RF coils in parallel receive mode uses the second subset of the RF coils.

In some embodiments, the RF coils may comprise first, second, and third subsets of coils with no common coils, and the first subset is used to generate spatial encoding, the second subset is used to select a non-planar isofield slice, and the third subset is used in parallel receive mode to detect magnetic resonance signals.

In some embodiments, reconstructing MRI images from the parallel received magnetic resonance signals uses algebraic reconstruction.

BRIEF DESCRIPTION OF THE DRAWINGS

FIG. 1A is a perspective schematic view of one embodiment of an electromagnet according to an embodiment of the invention.

FIG. 1B shows another electromagnet design according to an embodiment of the invention.

FIG. 1C and FIG. 1D show the field distributions in the axial cross-section corresponding to the designs of FIG. 1A and FIG. 1B, respectively.

FIG. 2A and FIG. 2B show isocontour field profiles along the central line perpendicular to the coil planes produced by electromagnet coils FIG. 1A and FIG. 1B, respectively.

FIG. 3 is a schematic overview illustrating the main components of such an open magnet MRI system according to an embodiment of the invention.

FIG. 5 shows detail of a pulse sequence used in one of the small DAQ (data acquisition) steps of FIG. 4B.

FIG. 6A is a graph of the polarization of Mz for 10 different slices over time as the field is ramped up and down by modulating the current generating the $B_0$ field.

FIG. 6B is a graph of current level over time corresponding to the graph of FIG. 6A.

FIG. 6C shows the relative signal intensity for 10 slices moving from close to the magnet (slice 1) to 20 cm depth (slice 10) corresponding to the graph of FIG. 6B.

DETAILED DESCRIPTION

Figure 1E:
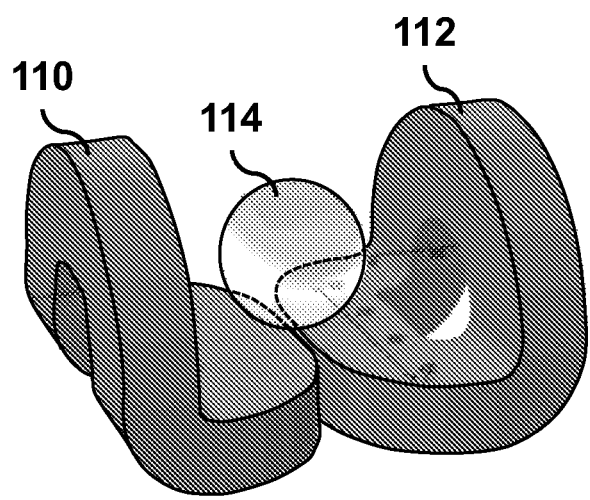
FIG. 1E is a perspective schematic view of another embodiment of an electromagnet according to an embodiment of the invention.

Embodiments of the present invention make practical, for the first time, MRI using a main magnet with a highly nonuniform field. This is made possible using techniques such as nonlinear MR imaging, field cycling MRI, RF based spatial encoding, and parallel imaging with algebraic reconstruction. FIG. 3 is a schematic overview illustrating the main components of such an open magnet MRI system according to an embodiment of the invention. The system includes a computer 300 that is connected to an electromagnet power supply 302, to an RF transmitter 310, and to an RF receiver 312. The power supply 302 is connected to an open geometry electromagnet 304 which generates a nonuniform magnetic field in an imaging region 306. The electromagnet 304 preferably comprises one or more resistive coil elements. An open geometry in the present description is defined to mean that the magnet does not completely surround the imaging region 306, e.g., it surrounds the center of the region by at most 270 degrees. The RF transmitter 310 and RF receiver 312 are connected to one or more arrays of RF coils 308 positioned near the imaging region 306.

In operation, the computer 300 controls the power supply 302 to change the current flowing through the electromagnet 304 so that the nonuniform magnetic field in the imaging region 306 ramps up and down. The computer 300 also controls the RF transmitter(s) 310 to use coil arrays 308 to perform slice selection, to generate excitation and refocusing pulses, and to perform spatial encoding. Numerous pulse sequences can be employed to generate different image contrast and spatial resolution in the imaging region 306. RF coils 308 are also used to detect magnetic resonance signals in the imaging region 306. The RF receiver and data acquisition system 312 receives the signals from the RF coils 308, and the computer 300 processes the received signal information from the RF receiver 312 to reconstruct a magnetic resonance image of an object in the imaging region 306. We now discuss these components and methods of the MRI system in more detail.

Main Magnet Design

In one embodiment of the invention, the main magnet uses a resistive electromagnet that produces a nonuniform magnetic field $B_0$ that can be ramped up and down rapidly. In this MRI system the field is purposefully nonuniform and asymmetric, and the imaging region 306 is adjacent to the coil elements in the electromagnet 304 that generates the main field. The system uses no additional gradient coils for spatial encoding other than the nonlinear gradients of the nonuniform main $B_0$ field but instead takes advantage of RF for spatial encoding combined with parallel receiver technology. This allows the design of the magnet to be open, simplifies construction criteria, and yields a silent imaging device. In the present description, a nonuniform field is defined to mean a field with more than 5 ppm variation with respect to changes in spatial location in an imaging region. The field gradient of a nonuniform field could be linear or nonlinear. An advantage of the present approach is that the gradient is not required to be linear.

FIG. 1A is a perspective schematic view of one embodiment of an electromagnet according to an embodiment of the invention. The electromagnet is composed of two rectangular (36×36 cm) resistive coil elements 100 and 102 without iron core inserts. Each coil element has 400 loops of hollow 4×4 mm² wires (in a 20×20 wire configuration). The two loops of wire may be built on a 3D-printed former structure made with gypsum material, which is strengthened with cyanoacrylate "color bond" infiltration. Hollow conductor wires are wound in the grooves of the former and held in place with thermal conductive epoxy. Hollow conductors can provide very high cooling efficiency because of larger cooling interface within the conductors. Electrical and coolant connectors are mounted on the side of the main magnet for external connections.

The two coil elements 100 and 102 are positioned in planes oriented at small angles relative to each other, so as to enhance the field at depth. FIG. 1B shows another embodiment of an electromagnet, also composed of two resistive coils 104 and 106 without iron core inserts (permanent magnets can be inserted inside these coil elements to provide higher field at depth). In this embodiment, each of the square coils has a slight bend inward at its midpoint to further enhance the field at depth. With 250 A DC current injected in these resistive coils, a $B_0$ field of 0.2 T can be generated at 20 cm depth, and a $B_0$ field is highest at the coil surface.

Different designs yield different maximum depth of field hence FOV in the direction perpendicular to the coil elements with different degrees of openness. FIG. 1C and FIG. 1D show the field distributions in the axial cross-section corresponding to the designs of FIG. 1A and FIG. 1B, respectively. By increasing the curvature of the coil elements we can generate the outer 0.1 T field line at sufficient depth for more than 30×30×20 cm imaging region with the main $B_0$ ranging from 0.6 T at the coil surface to 0.1 T at the outer line. FIG. 2C shows the field strength for each of the two designs of FIG. 1A and FIG. 1B as a function of depth, with approximately 0.6 T near the surface of the magnet and dropping to 0.1 T at approximately 25 cm depth, providing a depth of penetration similar to that of high frequency ultrasound. These field examples are not fixed, and more or less field strength can be obtained with different designs, coil windings, and current in the coils.

Figure 1F:
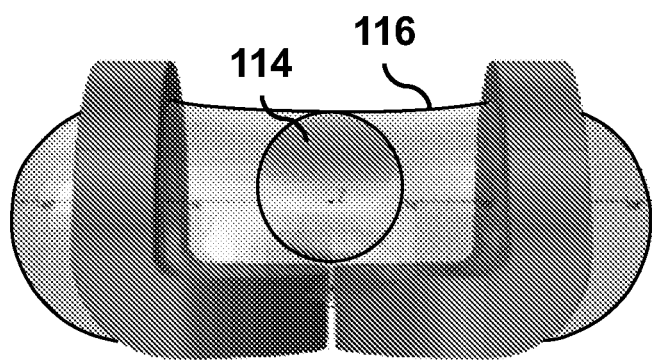
FIG. 1F is another view of the magnet of FIG. 1E showing the magnet's 0.2 T field line.
Figure 1G:
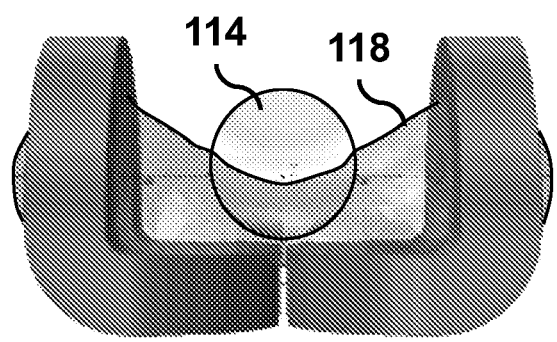
FIG. 1G is another view of the magnet of FIG. 1E showing the magnet's 0.1 T field line.
Figure 2C:
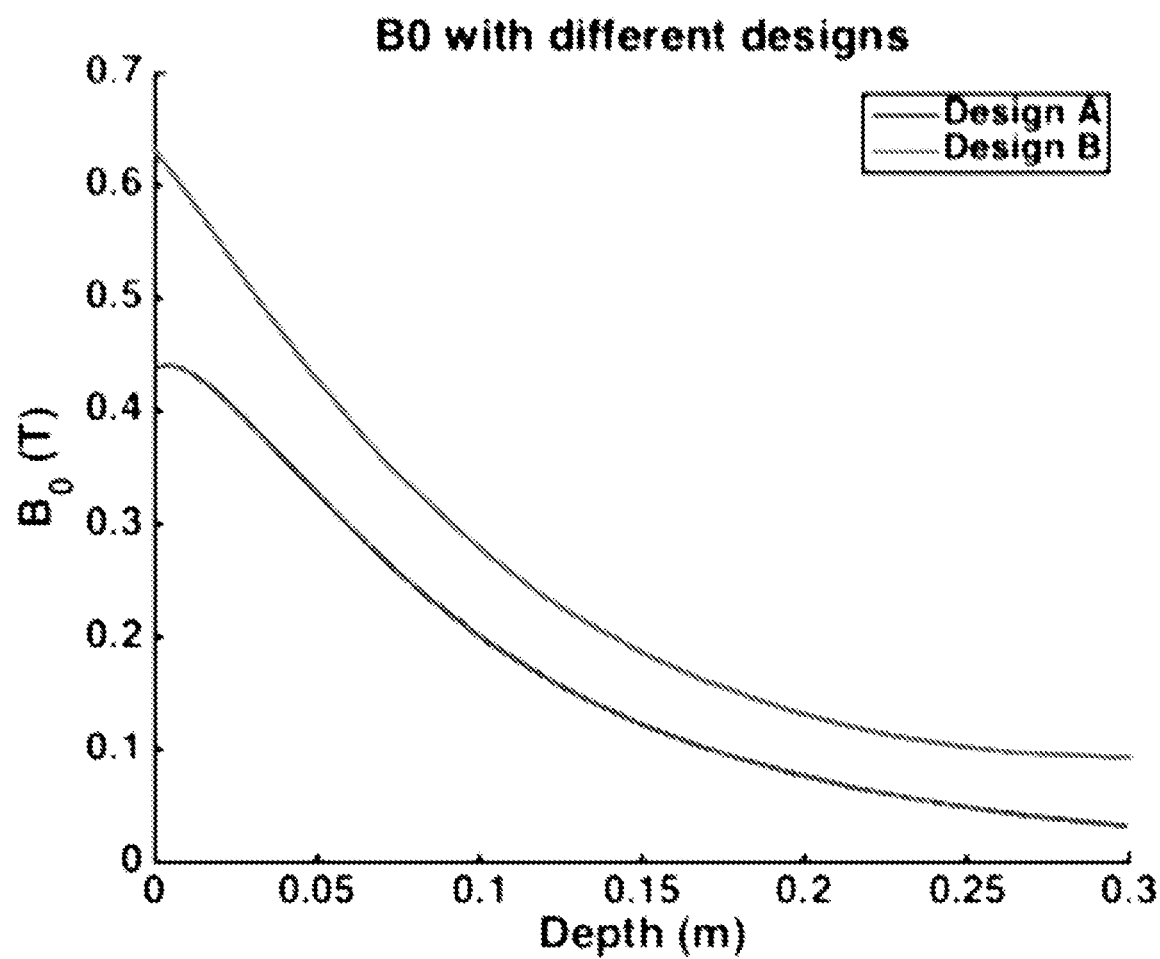
FIG. 2C shows the field strength for each of the two designs of FIG. 1A and FIG. 1B as a function of depth.

FIG. 1E is a perspective schematic view of another embodiment of an electromagnet according to an embodiment of the invention. This electromagnet is composed of two circular resistive coil elements 110 and 112. Each of the circular coils is bent inward at its midpoint by 90 degrees to further enhance the field at depth in the 20×20 cm imaging region 114. The magnet's 0.2 T field line 116 is shown in FIG. 1F and the 0.1 T field line 118 is shown in FIG. 1G.

FIG. 2A and FIG. 2B show isocontour field profiles along the central line perpendicular to the coil planes produced by electromagnet coils FIG. 1A and FIG. 1B, respectively. Each isocontour corresponds to a slice shape, which is a curved surface rather than a plane. Thus, in the context of this description, a slice is not a plane but a non-planar surface. These isofield surfaces are the basis for slice-selective imaging with non-planar slices.

Because the particular shape of the nonuniform field is not critical, there is considerably flexibility in the magnet construction and design. For any given design, however, the magnet's field is accurately mapped so that this information can be used in reconstruction. First, the shape of the static field is characterized. Second, the trajectory of field changes as the current is ramped between high and low is characterized. Like the shape of the field, the shape of this particular trajectory is not critical but it should be reproducible. The $B_0$ field can be characterized using a magnetic field meter (e.g., SENIS: Magnetic Field Mapping System) that uses a 3-axis Hall probe to map points in the imaging region. The $B_0$ field is recorded at each location, and entire field can be interpolated from these discrete $B_0$ samplings. The $B_0$ map will be used to determine the polarization strength of MRI signals as a function of distance from the coil loops and to characterize slice profiles as a function of depth and location in the imaging region.

During imaging, the electromagnet is ramped up and down rapidly by adjusting the current in the electromagnet using a power amplifier with outstanding stability and ramp control. The effect of ramping is to move the position of the isofield slices through the imaging region. In particular, if imaging is to be performed using protons at 4.26 MHz the position of the 0.1 T isofield slice (on resonance) is moved through the entire imaging region by adjusting the current in the electromagnet. For imaging, each slice is acquired at 0.1 T. Polarizing the spins at a higher field provides more magnetization to work with and hence higher signal strength, while imaging at a lower field reduces the amount of dephasing from the main field ($B_0$) nonuniformities and yet is still in the range where sample noise dominates over receiver coil noise. Thus, at full current, the 0.1 T slice is at maximal depth. As the electromagnet current is ramped down, the 0.1 T isofield slice is moved in, closer and closer to the magnet. Because all imaging is at a fixed target field of 0.1 T, the excitation and receiver RF coils are tuned to a fixed resonance frequency (in this case 4.26 MHz), and there is no need for adjusting the RF frequency across a broad range of field strengths (from 0.6 T to 0.1 T). This makes tuning the RF easy and also greatly reduces SAR problems that would otherwise be encountered with variable resonance frequency RF coils. As will be described in further detail below, the controlled B0 ramping between the high and low field condition can be ramped in discrete steps, each lasting on the order of tens of milliseconds. It should be emphasized that the high field may be larger than 0.3 T and the low field may be smaller than 0.1 T.

Design of the RF System

The RF system includes an array of multiple loop coils. In a preferred embodiment, a 3×3 transmit and receive RF phased array 308 of loop coils is used, with the geometry as shown in FIG. 3. These coils are used for a) slice selective spin excitation and refocusing pulses, b) spatially encoding the images using the Bloch-Siegert shift, and c) performing parallel receive of the MR signals for additional spatial encoding to aid image reconstruction. In this embodiment, the same array of coils is used for all of these purposes. Alternatively, some coils may be used for only one or two of these purposes. For example, RF excitation pulses may be transmitted from a single dedicated RF coil or from the entire array coils, acting in phase, separate RF coils can be used for spatial encoding, and a different set of RF coils could be used as receiver coils.

Each coil element in the array 308 has a diameter of 12 cm and the distance between loop centers is 10.5 cm. Each of these receiver elements has a spatially specific sensitivity region, the knowledge of which is incorporated into the image reconstruction algorithm. The array is positioned immediately above the center of the main magnet 304. Alternatively, the array 308 could be placed on top of the imaging subject in order to enhance both the parallel imaging spatial encoding as well as the SNR at depth. The coils are tuned to 4.26 MHz (corresponding to 0.1 T) and Bloch-Siegert encoding is applied off-resonance (e.g., at 60 kHz off resonance), providing reasonable SNR and efficiency. It is envisioned that SNR at depth and parallel imaging efficiency may be improved significantly with an additional flex-Rx-coil array on the side of the subject opposite the main field. Also, other coil designs could lead to simultaneous multi-slice imaging at different field strengths thereby greatly speeding up the acquisition time for multiple slices.

In operation, because imaging of a slice is done at low frequency of 4.26 MHz (corresponding to 0.1 T), the RF coil efficiency is maximized while minimizing the effects of $B_0$ field nonuniformities. Slice selection is done using RF excitation at this low frequency of 4.26 MHz, and changing the current in the electromagnet to move the 0.1 T (4.26 MHz) non-planar slice to different locations within the imaging region. Slice selectivity is determined by the resonance frequency/bandwidth of the RF pulses.

Since the gradient of the field changes with depth we can either have fixed bandwidth and variable slice thickness or vary the bandwidth of the excitation pulses with depth. Also note that the change in the $B_0$ direction at the edges of the imaging region and the change in the direction of the slice edges naturally limit the imaging region or sensitive volume from which we can image. Techniques similar to those of nonlinear imaging with O-space or Null space imaging can be used to reconstruct images from nonlinear projections (or nonlinear phase encoding) and nonlinear slice profiles.

The RF excitation signals transmitted from the coils 308 impose phase on the spins in the 0.1 T imaging slice. This could be done using various methods. Exploiting the Bloch-Siegert shift is a preferred approach to imposing phase on the spins. Using the Bloch-Siegert shift for spatial encoding allows us to eliminate the gradient coils which are typically necessary in MR devices, provides silent imaging capabilities, and when combined with parallel receiver coils and algebraic reconstruction, will provide high resolution imaging capabilities.

Different linear and nonlinear phase patterns could be imposed via the Bloch-Siegert shift by transmitting from different pairs of RF coils designed for this purpose. These coils will impose nonlinear phase patterns across the slice that can then be decoded during reconstruction to localize the spins. The spatial encoding from nonlinear gradient fields and RF can then be combined with parallel receiver coils to reconstruct MR images of the volume. These may or may not be reformatted into planar views via post-processing algorithms.

Previous applications of RF spatial encoding using the Bloch-Siegert shift have been aimed at generating linear phase encoding patterns in conventional MRI systems. In the present approach, on the other hand, the RF spatial encoding using the Bloch-Siegert shift is specifically designed to take advantage of the naturally nonlinear nature of the phase shifts produced in this magnet configuration with different combinations of coil elements. This application of nonlinear phase encoding RF pulses with different combinations of coil elements in the transmit array is a unique encoding strategy.

The RF transmitter 310 and receiver 312 in FIG. 3 may be implemented as a single instrument for RF signal generation and receiving. For example, a parallel transmit cabinet (consisting essentially of multiple power amplifiers) may be used for RF signal generation, modulation, and transmission. For excitation, the nine coil elements of array 308 will transmit together. For Bloch-Siegert encoding, subsets of two or more coil elements from an array of RF coils 308 could be electronically selected to generate each Bloch-Siegert pulse shape. All receiver coil elements 308 are then used for receiving the MR signal.

The receive system has a transmit/receive switch, preamplifier, and directly digitizes at the Larmor frequency. The data will be processed in a dedicated FPGA, which could detect any frequency errors and calculate a correction, which would be summed with the current demand prior to the amplifier to pull it back to the desired magnetic field. Using a water sample doped to reduce the T1 (longitudinal relaxation time) would allow field mapping data to be collected, processed and applied for each field step in the main field electromagnet current. In addition, once instabilities are characterized for a given pulse sequence, it will be possible to hard code any required correction fields directly in the dynamic controller.

Design of Pulse Sequences in the Presence of a Strong Gradient

In the past, MRI has not been performed in nonuniform $B_0$ fields because of the rapid dephasing that occurs in the presence of such field gradients. To overcome this problem, the present approach uses an electromagnet that is capable of field cycling. The use of field cycling in this MRI application allows the field to be reduced during the image acquisition interval, thereby minimizing intravoxel dephasing during readout. With all imaging (excitation, spatial encoding and receiving) performed at low field, the dephasing problem is greatly reduced. The Bloch-Siegert pulses are also applied in the presence of a very low field keeping SAR very low. The Bloch-Siegert pulses could be employed continuously during readout (since they are off-resonant) much in the same manner as the readout x-gradient in conventional MRI. In addition, 180-degree RF pulses may be inserted to refocus the effects of the residual static gradient fields. Multiple 180-degree RF pulses may be employed as in conventional MRI to create multiple spin echoes each of which refocuses the residual field gradients.

Polarization of spins occurs on the order of the rate of T1, and by using an electromagnet in which the field can be increased and decreased we gain substantial flexibility in multiple avenues. The advantages of the field cycling include: 1) the application of a high field for maximum signal (maximum spin polarization); 2) control of the polarization duration, which provides a mechanism for manipulating T1 contrast (unavailable with fixed field systems); and 3) low field for excitation RF and readout. The low field for readout then has additional advantages of lessening the effects of the nonuniform main field, and when combined with refocusing RF pulses can bring everything into phase and form echoes without the application of magnetic field imaging gradients. The low field also has the advantage of reduced RF power for both the excitation and spatial localization RF pulse sequences.

For the purposes of illustration, we now discuss three potential pulse sequences of a typical $B_0$ cycling. FIG. 4B illustrates a pulse sequence ramping up, FIG. 6B illustrates ramping down, and FIG. 7B illustrates returning to maximum field between each encoding cycle. The first two approaches are designed to require minimal ramping of the field while imaging each slice at the same resonance frequency. The third approach relies on maximal main field ramping to achieve as much polarization as possible for each slice.

Figure 4A:
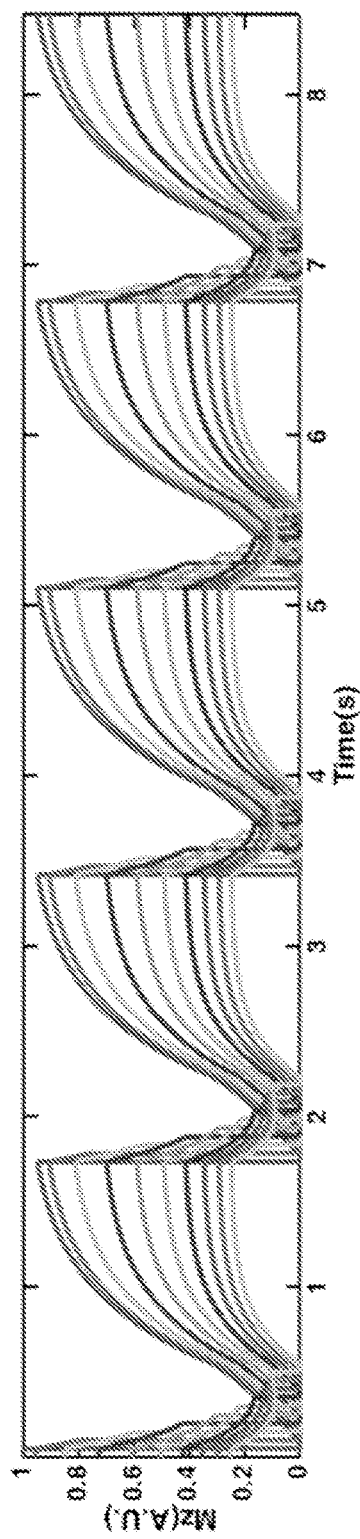
FIG. 4A is a graph of the polarization of Mz for 10 different slices over time as the field is ramped up and down by modulating the current that generates the $B_0$ field.
Figure 4B:
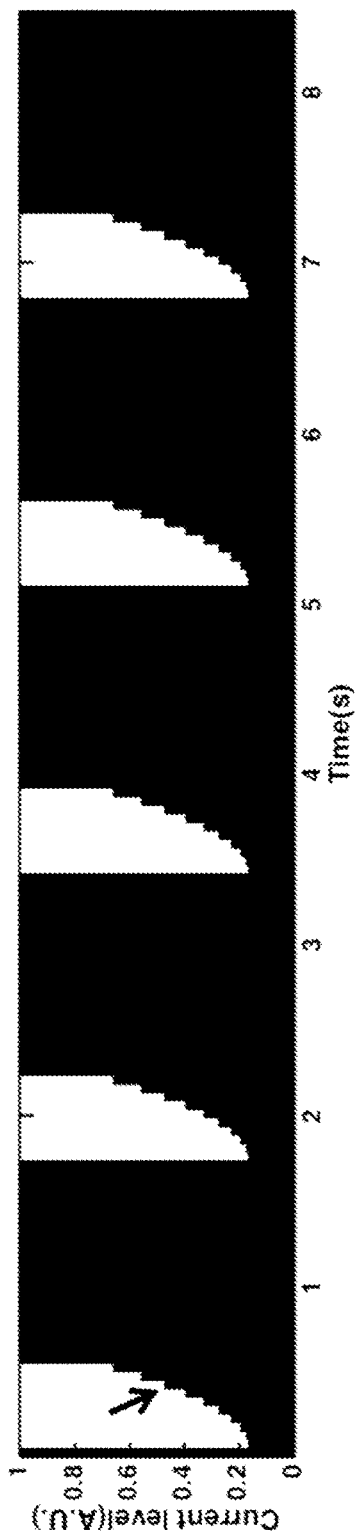
FIG. 4B is a graph of current level over time corresponding to the graph of FIG. 4A.

FIG. 4A is a graph of the polarization of Mz for 10 different slices over time as the field is ramped up and down by modulating the current that generates the $B_0$ field. FIG. 4B is a graph of this corresponding current level over time. Each line in FIG. 4A and step in FIG. 4B represents a different slice, and in this case there are 10 slices spanning the initial field strengths from 0.6 T to 0.1 T across the entire imaging region depth in Z (20 cm). Different lines in FIG. 4A represent the Mz magnetization history for different depths in the imaging region. The periods of maximum current occur during the spin polarization phase, while the periods of ramping up or down are the imaging phase.

Figure 4C:
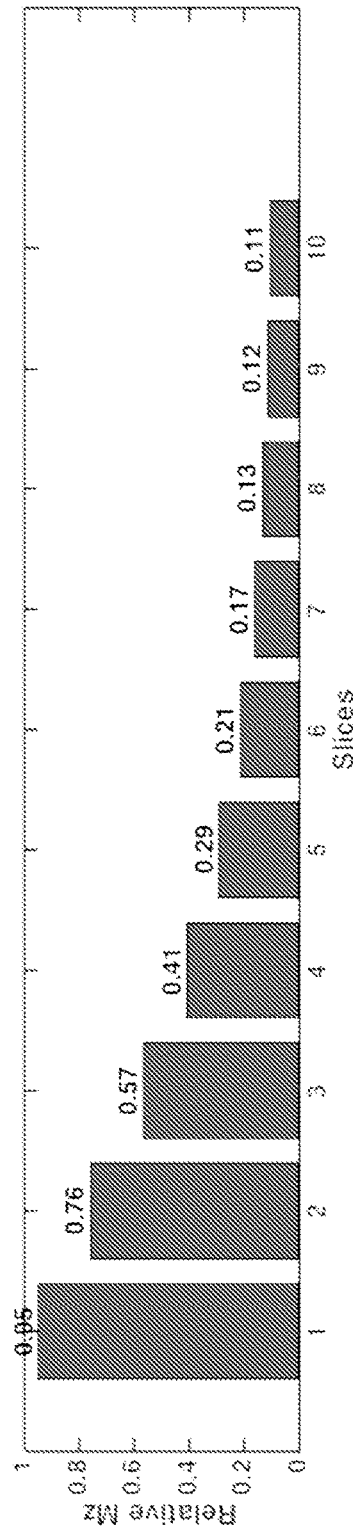
FIG. 4C shows the relative signal intensity for 10 slices moving from close to the magnet (slice 1) to 20 cm depth (slice 10) corresponding to the graph of FIG. 4B.

Image acquisition takes place between the 180-degree refocusing pulses shown in FIG. 4B, which is also when Mz drops to zero in FIG. 4A. The main field current is dropped to a different level for each slice (depending on the distance of the slice from the coil) such that each slice is acquired at 0.1 T (4.26 MHz in this particular example) resonance frequency. The graphs show the repetition of five encoding intervals over time, each having ten slices (the number of steps). For a complete imaging experiment there would be a larger number of these intervals (say 30 to 60 or more) with a different Bloch-Siegert encoding pulse shape for each interval. Not shown is an initial polarization interval of approximately 5 seconds or more (5 T1's). If we assume 2 seconds per polarization/readout cycle×60 cycles (with a different Bloch-Siegert pulse shape each cycle), this would yield a total imaging time of 2 minutes. Adding more slices could be done by increasing the number of steps within each polarization/readout cycle (at a cost of 50 ms per step while also impacting the signal and contrast) or adding additional cycles for different slices. In the latter case 20 slices could be done in 2 sets of 60 cycles hence doubling imaging time to 4 minutes. The field cycling can be manipulated to balance signal intensity across slices and/or to adjust the T1-weighting. Conventional TR (repetition time) is different here as Mz is new each time and mostly only accumulating when the polarization field is on. On a conventional MRI system the field is fixed (say at 3 T) and never changed. FIG. 4C shows the relative signal intensity for 10 slices moving from close to the magnet (slice 1) to 20 cm depth (slice 10). There is a decrease in signal because of the decreased field (and hence polarization) at depth.

FIG. 5 shows detail of a pulse sequence used in one of the small DAQ (data acquisition) steps of FIG. 4B. Specifically, it shows spin echo imaging sequence with Bloch Siegert encoding in readout mode and blipped mode. Within each small ramping step in $B_0$, the field for the slice of interest is 0.1 T and spin echo imaging can be performed with Bloch-Siegert RF spatial encoding. While there are many ways to do this, a T1-weighted (from the polarization period) encoding scheme could use 16 or more Bloch-Siegert pulses (a single Bloch-Siegert pulse shape is used for each readout) and 256 or more readout points can be collected between 180-degree refocusing pulses. A complete data matrix is then composed of echoes of 256 points, with 16 or more different Bloch-Siegert pulse shapes for each readout, analogous to nonlinear projections in O-space imaging). Thus the single 50 ms step shown in FIG. 5 would be repeated 16 or more times with a different Bloch-Siegert pulse shape between each echo. Algebraic reconstruction is then used to reconstruct a 128×128 or 256×256 image (matrix size can very over a much larger range) for each slice. There are as many ways to do this, as there are conventional MRI pulse sequences. Other pulse sequences are possible along the lines of turbo-spin-echo with multiple 180's (low SAR because of the low field) providing maximal signal in the presence of this constant low field gradient. The readouts can be shifted in time to increase T2 weighting. The Bloch-Siegert encoding for a given pulse shape is wound up with successive pulses much like phase encode gradients and thus there is a zero crossing in the Bloch-Siegert encoding (at the center of each echo) that would contribute maximally to contrast just as in EPI (echo-planar imaging) or turbo-spin echo sequences. The Bloch-Siegert shift encoding is explained in more detail below.

Another scheme is to image as the field is cycled down. This strategy provides maximally uniform signal across all slices by improving SNR for the deepest slices (slice 10 and neighbors) and decreasing signal for the slices closest to the electromagnet (slice 1 and neighbors) by manipulating the imaging time of each slice relative to the polarization time. FIG. 6A is a graph of the polarization of Mz for 10 different slices over time as the field is ramped up and down by modulating the current generating the $B_0$ field. FIG. 6B is a graph of this corresponding current level over time. Each line in FIG. 6A and step in FIG. 6B represents a different slice, and in this case there are 10 slices spanning field strengths from 0.6 T to 0.1 T across the entire imaging region depth in Z (20 cm). As we saw in FIG. 4B, the polarization field is dropped to its minimum and the slice closest to the electromagnet (highest polarization field) is acquired first. Subsequent slices (moving away from the device) are acquired as the field is ramped up. In FIG. 6B, slice 10 (furthest away) is acquired first to take full advantage of maximum polarization (since this decays with T1) and the subsequent slices are sequentially acquired moving inward towards the device. This provides more uniform signal across the depth of imaging region (slices) at the expense of signal in the closest slices. Imaging is performed at 0.1 T at each step using the scheme shown in FIG. 5. FIG. 6C shows the relative signal intensity for 10 slices moving from close to the magnet (slice 1) to 20 cm depth (slice 10).

Figure 7A:
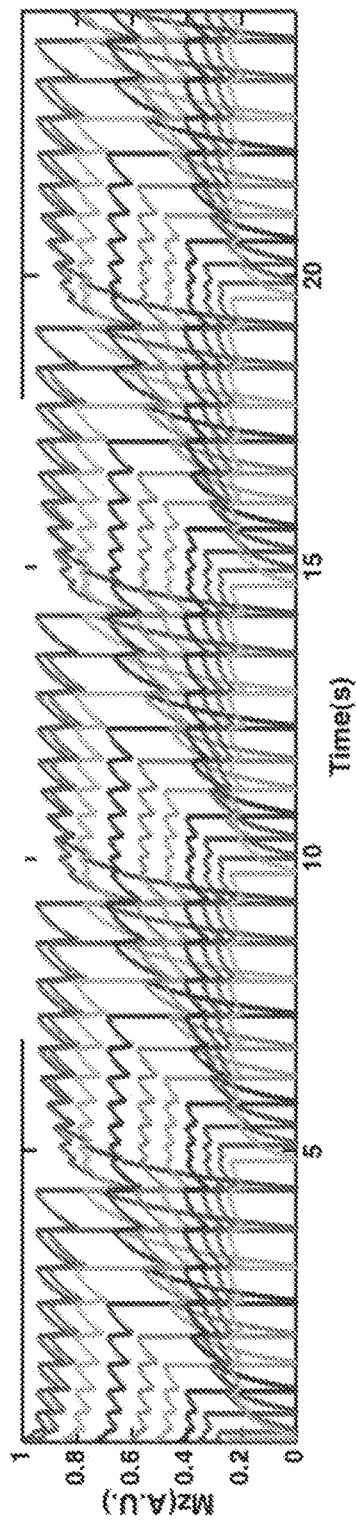
FIG. 7A is a graph of the polarization of Mz for 10 different slices over time as the field is ramped up and down by modulating the current generating the $B_0$ field.
Figure 7B:
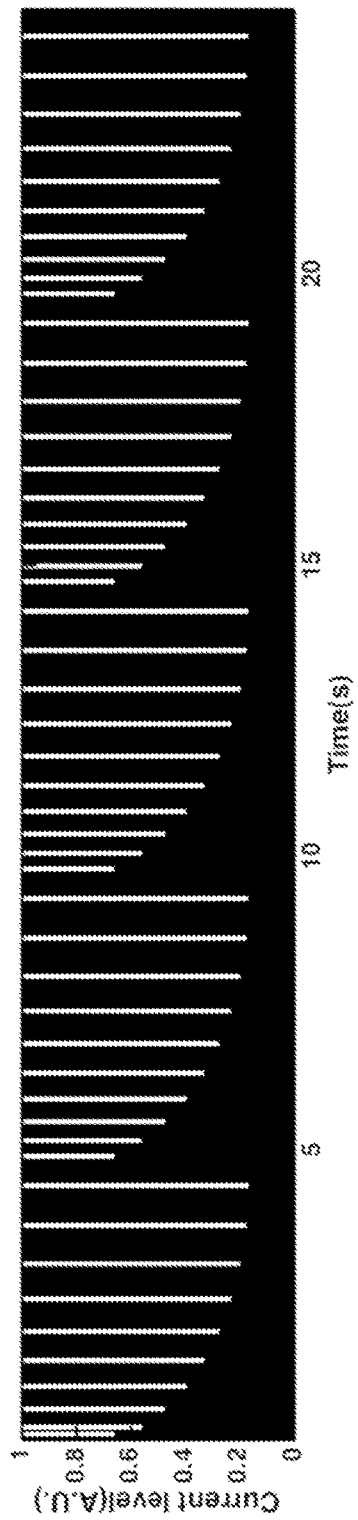
FIG. 7B is a graph of current level over time corresponding to the graph of FIG. 7A.
Figure 7C:
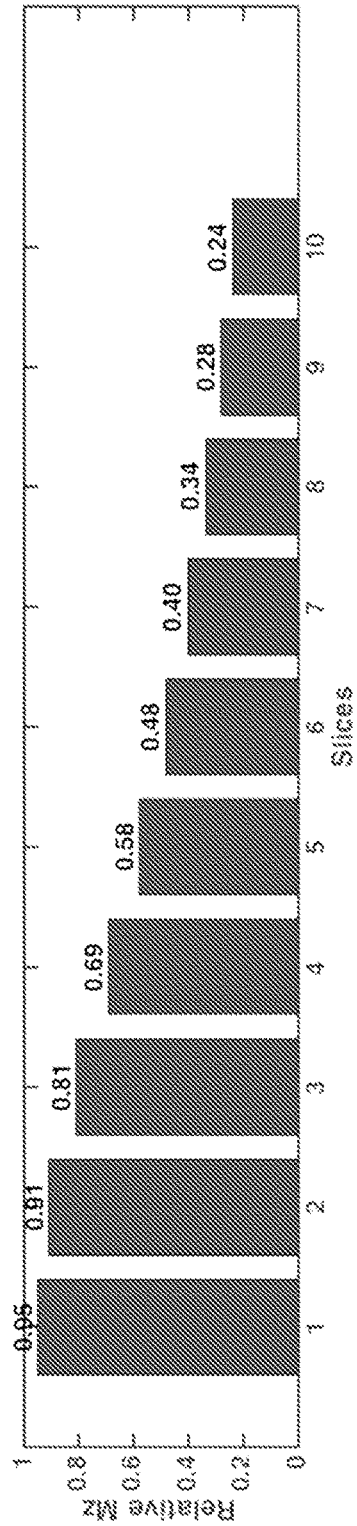
FIG. 7C shows the relative signal intensity for 10 slices moving from close to the magnet (slice 1) to 20 cm depth (slice 10) corresponding to the graph of FIG. 7B.

Finally, as shown in FIG. 7A, FIG. 7B, FIG. 7C, if we use the ramp down strategy such that each slice is acquired at 0.1 T, but return the main field to full pre-polarization strength between each slice acquisition, we can maximize the signal for all slices. In this scheme, the data is acquired in steps (during the white vertical lines in FIG. 7B) when the current to the main magnet is adjusted such that the slice of interest is at 0.1 T. This scheme puts maximum demands on the power amplifier in terms of ramping but also provides maximum SNR for all slices. The Mz across such a scheme is complicated as each slice sees a different field over time but the net result is better signal across the volume.

In conventional MRI excitation the RF field is generally perpendicular to the main field $B_0$ for maximum efficiency. In the present design the main field direction changes across the field of view and thus we need to compute the components of the RF field perpendicular to the main field $B_0$. Specifically, we project the RF field onto a set of new bases established on the unit vector of $$B_0(r): B_{0e}(r) = (B_{0ex}, B_{0ey}, B_{0ez}) = B_0(r)/|B_0(r)|$$

$$w = \frac{B_0(r)}{|B_0(r)|}, u = \frac{(0, B_{0ey}, B_{0ez})}{|0, B_{0ey}, B_{0ez}|}, v = w \times u$$

With the RF field $$B_1(r) = (B_{1x}, B_{1y}, B_{1z})$$

created by each loop coil, $B_1+$ in the positively-rotating frame and $B_1^-$ in the negatively-rotating frame perpendicular to the main field $B_0$ are $$B_1^+ = \frac{B_1(r) \cdot u + 1j \cdot B_1(r) \cdot v}{2} \quad B_1^- = \frac{(B_1(r) \cdot u - 1j \cdot B_1(r) \cdot v)^*}{2}.$$

The overall $B_1^+$ field affects the flip angle during the spin excitation and is composed of $B_1^+$ fields from the individual RF coils weighted by the currents $$B_1^+ = \Sigma I_c \cdot B_{1c}^+$$

We can tune the current level and phase on each of the RF transmit coils such that it generates a near-uniform excitation in the central region of the slice. $B_1^-$ determines the receive sensitivity for individual coils, which are used in the parallel reconstruction and provides spatial encoding based in part on this receiver profile.

Design Bloch-Siegert Nonlinear Spatial Encoding

Since there are no conventional linear x, y, z-spatial encoding imaging gradients associated with this MRI system, spatial localization is provided using RF to generate phasors and parallel receive to assist the spatial encoding. The Bloch-Siegert shift approach has previously been developed to provide linear spatial encoding analogous to conventional phase encoding in Fourier transform based MRI.

Applying an off-resonance RF pulse, RF ($\omega_{off}$), during the readout produces a frequency shift $\omega_{BS} = (\gamma B_1)^2 / \omega_{off}$ when $\omega_{off} \gg \gamma B_1$, which introduces phase variations across the slice. These phase shifts can be imposed in different patterns sufficient for spatial encoding. This frequency can be used for encoding because of inherent variations of $B_1$ intensity across the imaging space. The encoding coefficient for a voxel at r can be expressed as $E(r, t)=e^{j\omega_{BS}(r)t}$ as a function of time t. Because the Bloch-Siegert pulses are imposed off resonance, it is possible to apply these pulses simultaneous during readout analogous to imposing a conventional readout gradient in a conventional gradient or spin echo imaging experiment.

In our approach, we produce different phase windings (phasor shapes) across the slice by varying the coil-element combinations used to transmit the Bloch-Siegert pulses. Different combinations of two (or more) RF coils from the RF array are selected in successive repetitions (polarization and imaging cycles) to provide differential phase encoding across the slice.

Figure 8:
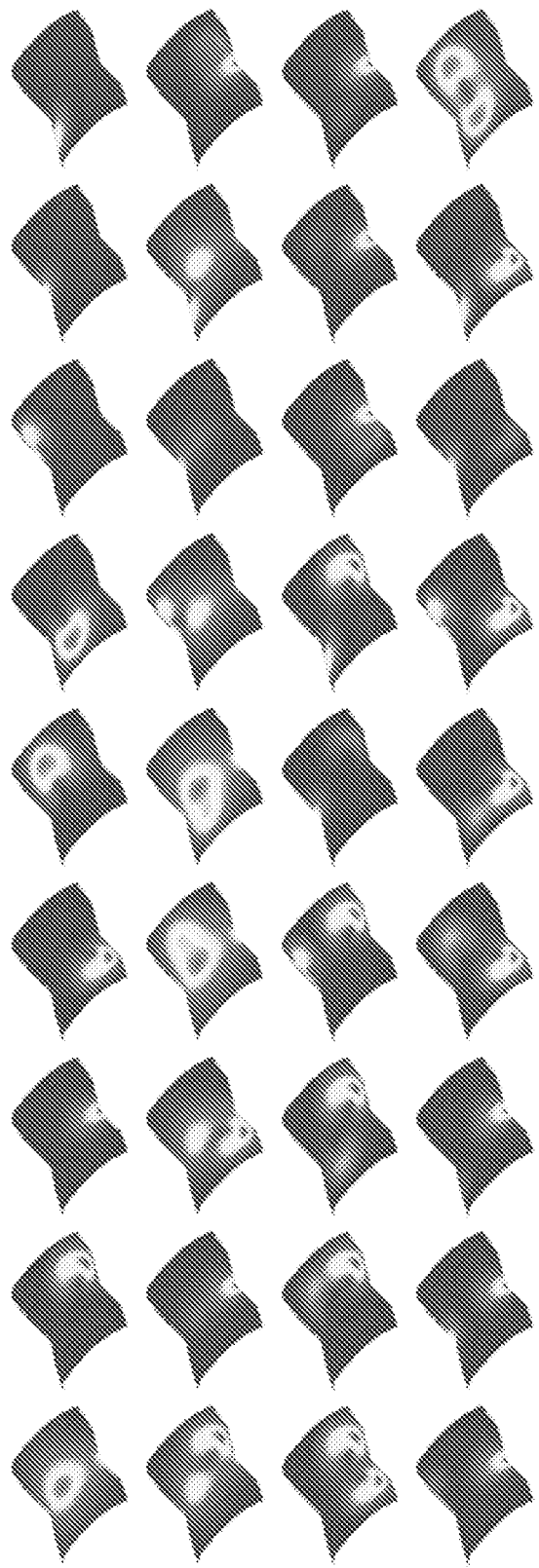
FIG. 8 shows the initial Bloch-Siegert phasors for 36 different combinations of coils with 10 A and 0-degree phase current driving each of the elements.

Different combinations of RF coils elements simultaneously carry currents at the same off-resonance frequency but with different amplitudes and phases thereby varying the encoding pattern across the slice. These combinations of coils produce different initial phasor patterns, which then evolve with subsequent Bloch-Siegert pulses across the acquisition window. With multiple coil elements, there are many combinations that can be chosen to produce different initial phasors, which are allowed to evolve with time. The initial Bloch-Siegert phasors for 36 different combinations of coils (1 or 2 out of the 9 elements) with 10 A and 0-degree phase current driving each of the elements are shown in FIG. 8. These are starting phasors for a single slice across multiple cycles of polarization and imaging. These phasors together with the sensitivity profiles of the receiver coils are then used to spatially localize signals and generate images using algebraic reconstruction. The initial phasor in FIG. 8 is further wound by continuous application of the Bloch-Siegert pulses in the pulse sequence shown in FIG. 5. This is analogous to a readout gradient in conventional MRI, but in this case imposing nonlinear phase variations across the slice. Successive B-S pulses have different initial patterns (because different pairs of coils are used to generate the pulses). Each of the different starting phase patterns could be allowed to evolve across the readout while sampling the echo that is formed. With phasors as known factors in a an algebraic reconstruction approach, such data can be used to form an image.

Using a given pulse sequence, and 9 receiver coils, the 36 different Bloch-Siegert phasor shapes shown in FIG. 8 and a total of 128 different windings of each of these phasors results in an acquisition of a data matrix of 128×36×9 for each slice, from which we can reconstruct a 128×128 image. This acquisition may be done, for example, using a polarization period of 5 seconds followed by a 32-echo multiecho acquisition with 128 data points recorded per echo, for each slice as in FIG. 5. The slices can then be reformatted into axial or sagittal views but the in-plane (nonplanar slice) views would typically have the best spatial resolution.

It should be noted that the pulse sequences described above are examples only. Many others are possible, using different polarization schemes, different polarization intervals, echo trains of different lengths, multiple 180 s, or acquisitions centered at later times (80 ms). Like any other MR approach, resolution can be improved with more data collection as can SNR. SNR can also be further improved with additional receiver coil elements both within the device but also with a flexible receiver arrays placed on the sides and top of the patient opposite the device. Additional SNR could be gained by using a higher $B_0$ field strength, which could potentially be achieved simply with more current in the main field electromagnet or with different coil designs.

Many pulse sequences are possible, just as in conventional MRI, and thus contrast mechanisms of conventional MRI are available. There is an additional free parameter that can be used to generate T1 contrast through the timing of the field cycling of the electromagnet (and hence polarization timing/history for the spins). Conventional pulse sequences such as asymmetric spin echo, turbo-spin-echo, and inversion recovery imaging are all available.

Simultaneous multislice imaging wherein multiple slices are obtained simultaneously is also envisioned in order to increase data acquisition efficiency. Another formulation could see swept RF pulses in synchrony with sweeping the field from max to min and exciting/encoding the slices in a continuous manner.

All the synchronization, triggering and timing of individual components is controlled with a computer 300 (FIG. 3). The computer preferably includes multiple graphic processing units (GPUs) to rapidly reconstruct images using an algebraic reconstruction algorithm.

Implementations

There are a variety of possible realizations and applications of an MRI system according to the present invention. These implementations can take advantage of this open, one-side imaging system. They can also take advantage of the compact size and low cost relative to conventional MRI systems. For example, in one implementation, the magnets may be embedded under an examination table such that they are moveable over the length of the table. With patients laying in supine, prone or a lateral position on top of the table, the imaging system may be moved on rails under the table such that it can move up and down the length of the table depending upon the region to be imaged.

In another design the system could be built into a wall or along a rail for weighted spine imaging in which the patient stands leaning against the device. Other systems could be designed specifically for breast imaging or for head imaging in a chair head-rest. Such devices would benefit greatly if high temperature superconductors could be used for the primary electromagnet system.

Applications include neuroimaging, cardiac MR, body imaging including pelvic and abdominal MRI, angiography, breast screening, prostate imaging, gynecologic applications, and musculoskeletal imaging. It can also be used to guide interventional procedures.

This design also has the potential to be miniaturized to yield handheld MRI devices. Gynecologic and prostate imaging systems with invasive RF probes and electromagnets designed to fit the anatomy are also envisioned.

The invention claimed is:

1. A method for magnetic resonance imaging, the method comprising:
   using an electromagnet to generate a spatially nonuniform magnetic field within an imaging region;
   controlling current through the electromagnet to repeatedly cycle the nonuniform magnetic field between a first strength for polarizing spins and a second strength, lower than the first strength, for spatial encoding and readout;
   using RF coils to generate excitation pulses at a frequency that selects a non-planar isofield slice for imaging, and to generate refocusing pulses for imaging;
   using the RF coils to generate spatial encoding pulses, and using the RF coils in parallel receive mode to detect magnetic resonance signals originating from the selected non-planar isofield slice of the nonuniform magnetic field in the imaging region; and reconstructing MRI images from the parallel received magnetic resonance signals.

2. The method of claim 1 wherein the nonuniform magnetic field has a spatial variation of more than 5 ppm within the imaging region.

3. The method of claim 1 wherein the electromagnet is an open-geometry electromagnet that extends around the imaging region by no more than 270 degrees.

4. The method of claim 1 wherein the first strength for polarizing spins is at least 0.2 T and the second strength for spatial encoding and readout is at most 0.1 T.

5. The method of claim 1 wherein the first strength is at least 0.6 T and the second strength for spatial encoding and readout is at most 0.1 T.

6. The method of claim 1 wherein the spatial encoding is nonlinear spatial encoding.

7. The method of claim 1 wherein the spatial encoding is generated via the Bloch-Siegert shift or other spatial encoding pulses.

8. The method of claim 1 wherein the RF coils comprise a phased array of coils.

9. The method of claim 1 wherein using RF coils to generate refocusing pulses comprises inserting 180-degree RF pulses to refocus the effects of the residual static gradient fields.

10. The method of claim 1 wherein using the RF coils to generate spatial encoding comprises using a first subset of the RF coils, and using RF coils to select a non-planar isofield slice and using the RF coils in parallel receive mode to detect magnetic resonance signals uses a second subset of the RF coils.

11. The method of claim 1 wherein using the RF coils to generate spatial encoding comprises using a first subset of the RF coils, using RF coils to select a non-planar isofield slice comprises using a second subset of the RF coils, and using the RF coils in parallel receive mode to detect magnetic resonance signals uses a third subset of the RF coils, where the first subset, second subset, and third subset contain no common coils.

12. The method of claim 1 wherein reconstructing MRI images from the parallel received magnetic resonance signals uses algebraic reconstruction.

* * * * *